US012258546B2

(12) United States Patent
Hsu et al.

(10) Patent No.: US 12,258,546 B2
(45) Date of Patent: Mar. 25, 2025

(54) CELL AND TISSUE SHEET FORMING PACKAGE AND CELL INJECTION EQUIPMENT

(71) Applicant: Industrial Technology Research Institute, Hsinchu (TW)

(72) Inventors: Hsin-Yi Hsu, Taoyuan (TW); Yang-Cheng Lin, Chiayi (TW); Chao-Hong Hsu, Tainan (TW); Yu-Bing Liou, Hsinchu (TW); Li-Hsin Lin, Hsinchu County (TW); Hsin-Hsin Shen, Hsinchu County (TW); Yu-Chi Wang, New Taipei (TW); Chang-Chou Li, Tainan (TW); Chih-Hung Huang, Tainan (TW)

(73) Assignee: Industrial Technology Research Institute, Hsinchu (TW)

( * ) Notice: Subject to any disclaimer, the term of this patent is extended or adjusted under 35 U.S.C. 154(b) by 671 days.

(21) Appl. No.: 17/561,117

(22) Filed: Dec. 23, 2021

(65) Prior Publication Data
US 2023/0203415 A1    Jun. 29, 2023

(51) Int. Cl.
*B01L 3/00* (2006.01)
*C12M 1/00* (2006.01)
*C12M 1/42* (2006.01)
*C12M 3/00* (2006.01)

(52) U.S. Cl.
CPC ............ *C12M 21/08* (2013.01); *C12M 23/34* (2013.01); *C12M 29/06* (2013.01); *C12M 35/02* (2013.01)

(58) Field of Classification Search
CPC . C12N 2535/00; B01L 9/52; B01L 2300/045; B01L 2300/046
See application file for complete search history.

(56) References Cited

U.S. PATENT DOCUMENTS

| 5,310,676 A | 5/1994 | Johansson et al. |
| 5,730,721 A | 3/1998 | Hyatt et al. |
| 9,107,979 B2 | 8/2015 | Lin et al. |

(Continued)

FOREIGN PATENT DOCUMENTS

| CN | 108350420 A | 7/2018 |
| CN | 208136266 U | 11/2018 |

(Continued)

OTHER PUBLICATIONS

Extended European Search Report issued on Jun. 22, 2022.

*Primary Examiner* — Natalia Levkovich
(74) *Attorney, Agent, or Firm* — WPAT, PC

(57) ABSTRACT

A cell and tissue sheet forming package includes a container body, a membrane, a sliding door plate and a sealing film. The sliding door plate is disposed slidably on a top of the container body to cover or expose the membrane. The sliding door plate has a hole and a passive magnetic assembly. The cell injection equipment includes a carrier, an injection mechanism and a drive mechanism. The carrier carries the package, and the drive mechanism moves the carrier and the injection mechanism to have the injection mechanism to inject a solution, through the hole, into the package. A heating element of the carrier is introduced to heat the membrane and the solution to transform the solution into a colloid sheet on the membrane. Then, the positive magnetic assembly engages magnetically the passive magnetic assembly to slide the sliding door plate to expose the colloid sheet on the membrane.

11 Claims, 13 Drawing Sheets

(56) References Cited

U.S. PATENT DOCUMENTS

2006/0153815 A1    7/2006  Seyda et al.
2021/0324318 A1   10/2021  Parietti et al.

FOREIGN PATENT DOCUMENTS

| CN | 109609344 A | 4/2019 |
|---|---|---|
| CN | 211112043 U | 7/2020 |
| CN | 112210499 A | 1/2021 |
| CN | 213596305 U | 7/2021 |
| CN | 214029979 U | 8/2021 |
| CN | 114867836 A | 8/2022 |
| JP | S63196285 A | 8/1988 |
| JP | 2001299326 A | 10/2001 |
| JP | 2003070460 A | 3/2003 |
| JP | 2008022715 A | 2/2008 |
| JP | 2009201509 A | 9/2009 |
| JP | 4896494 B2 | 3/2012 |
| JP | 5781398 B2 | 9/2015 |
| JP | 2018033318 A | 3/2018 |
| JP | 2018121568 A | 8/2018 |
| JP | 2020536632 A | 12/2020 |
| TW | 200731957 | 9/2007 |
| TW | I753622 | 1/2022 |
| WO | WO98/24880 A1 | 6/1998 |
| WO | WO2018064778 A1 | 4/2018 |
| WO | WO2020242904 A1 | 12/2020 |
| WO | WO 2021/038996 A1 | 3/2021 |

CELL AND TISSUE SHEET FORMING PACKAGE AND CELL INJECTION EQUIPMENT

TECHNICAL FIELD

The present disclosure relates in general to a cell and tissue sheet forming package and cell injection equipment.

BACKGROUND

Cell and tissue sheets (or dressings for short) are commonly used in the medical field. By covering a wound with the cell and tissue sheet, healing speed of the wound would be increased.

Currently, a typical process for producing the cell and tissue sheets is roughly as follows. Firstly, cell collection is carried out. Then, a cell culture is performed, and further the cultured cells would be transported and stored for a subsequent surgery. However, in this process, the cell culture is extremely time-consuming and expensive because specific procedures and facilities in the laboratory are needed. As for the transportation, if the temperature, humidity and other environmental conditions are not properly controlled, then a risk of damage or contamination would be inevitable.

Accordingly, how to develop a "cell and tissue sheet forming package and associated cell injection equipment" that can simplify a cell therapy operation process, need no laboratory for culturing cells and cell membranes, waive the risk in transportation, and produce the cell sheet in situ through packaging and injection, is definitely urgent problem to be solved by those skill in the art.

SUMMARY

In one embodiment of this disclosure, a cell and tissue sheet forming package includes:

a container body, having a cavity;

a membrane, disposed in the cavity, made of a hydrophilic material; and a sliding door plate, disposed slidably at a top of the container body in a manner of being parallel to a horizontal level surface and a first direction, the sliding door plate being slidable between a first position and a second position at the top; wherein, when the sliding door plate is at the first position, the sliding door plate covers the cavity and the membrane; wherein, when the sliding door plate is at the second position, the cavity and the membrane are exposed; the sliding door plate including:

a hole, penetrating from a top surface of the sliding door plate to a bottom surface of the sliding door plate; wherein, when the sliding door plate, is at the first position, the hole is positioned above the cavity and the membrane for a solution to be injected therethrough into the cavity from the top surface of the sliding door plate; and a passive magnetic assembly, disposed at the sliding door plate for connecting magnetically a positive magnetic assembly, the positive magnetic assembly being configured to slide the sliding door plate; and a sealing film, configured to cover the sliding door plate and the container body so as to seal the sliding door plate and the membrane.

In another embodiment of this disclosure, a cell injection equipment, applied to the cell and tissue sheet forming package, includes:

a carrier, including:

a base block, configured to carry the cell and tissue sheet forming package;

a top block, disposed pivotally on the base block for positioning the cell and tissue sheet forming package inside the base block, further having an injection hole; wherein, when the top block is closed on the base block, a projection area of the injection hole and another projection area of the hole of the sliding door plate of the cell and tissue sheet forming package are overlapped;

at least one heating element, disposed at the base block for providing thermal energy to the membrane and the solution; and a positive magnetic assembly, disposed slidably between a third position and a fourth position at a top of the top block in a manner of being parallel to the first direction, configured to magnetically connect the passive magnetic assembly; wherein, when the positive magnetic assembly slides to the fourth position, the sliding door plate is slided synchronously to the second position;

an injection mechanism, including:

a fixing set, mounted on a rack extending in perpendicular to the horizontal level surface;

an injection assembly, including:

a tube body, configured to contain the solution, disposed at the fixing set by being perpendicular to the horizontal level surface;

an injection head, coaxially disposed to a bottom of the tube body, having an injection tip protruding toward the horizontal level surface; and a piston member, coaxially disposed in the tube body; and a drive mechanism, including:

a first drive assembly, configured to drive the carrier to undergo a reciprocating movement parallel to the horizontal level surface and the first direction between a fifth position and a sixth position; wherein, when the carrier is at the fifth position, a projection area of the injection head is deviated from another projection area of the injection hole of the top block; wherein, when the carrier is at the sixth position, the projection area of the injection head, the another projection area of the injection hole of the top block, and a further projection area of the hole of the sliding door plate are overlapped;

a second drive assembly, configured to drive the fixing set and the injection assembly to undergo another reciprocating movement along the rack perpendicular to the horizontal level surface between a seventh position and an eighth position; wherein, when the fixing set and the injection assembly are at the seventh position, a horizontal position of the injection tip is higher than that of a top surface of the top block of the carrier; wherein, when the fixing set and the injection assembly are at the eighth position, the horizontal position of the injection tip is lower than that of the sealing film on the hole of the sliding door plate; and a third drive assembly, configured to drive the piston member to move perpendicular to the horizontal level surface inside the tube body for pushing the solution out of the tube body via the injection head.

DETAILED DESCRIPTION

In this disclosure, with the cell and tissue sheet forming package and the cell injection equipment, since the cell sheets are produced on-site in the clinic, thus the cell treatment procedures can be simplified, no pre-work is required in the laboratory to culture the cells and further to form the cell sheets, and so the risk in temperature control during transportation can be effectively avoided.

Figure 1:
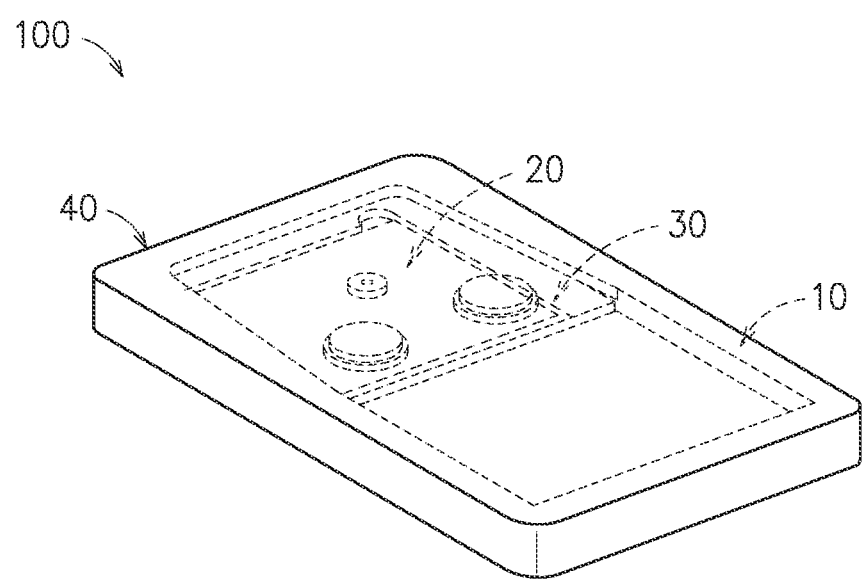
FIG. 1 is a schematic perspective view of an embodiment of the cell and tissue sheet forming package in accordance with this disclosure.
Figure 2:
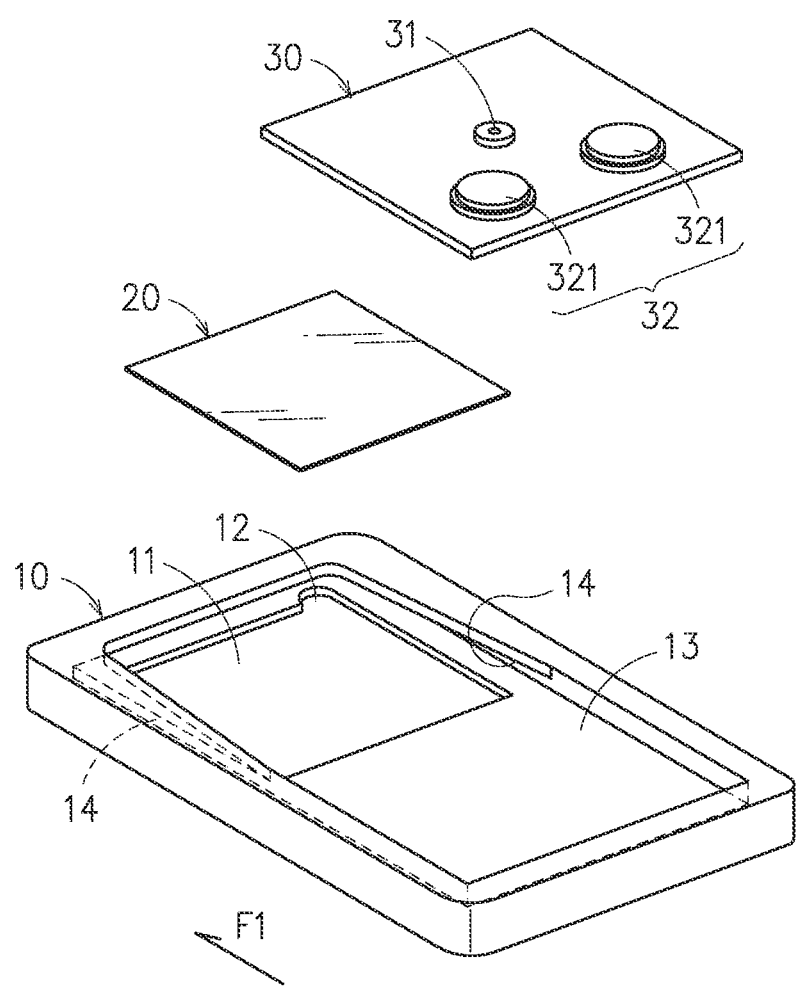
FIG. 2 is a schematic exploded view of FIG. 1 with the sealing film removed.

Referring to FIG. 1 and FIG. 2, a cell and tissue sheet forming package 100 includes a container body 10, a membrane 20, a sliding door plate 30 and a sealing film 40.

The container body 10 and the sliding door plate 30 can be made of one of PET, PS, PP, PVC, PE, PC, ABS and PTFE.

The membrane 20, as a hydrophilic material, can be made of one of PLA, PCL and collagen.

The sealing film 40 can be made of one of Tyvek, Al foil and nylon.

Figure 3:
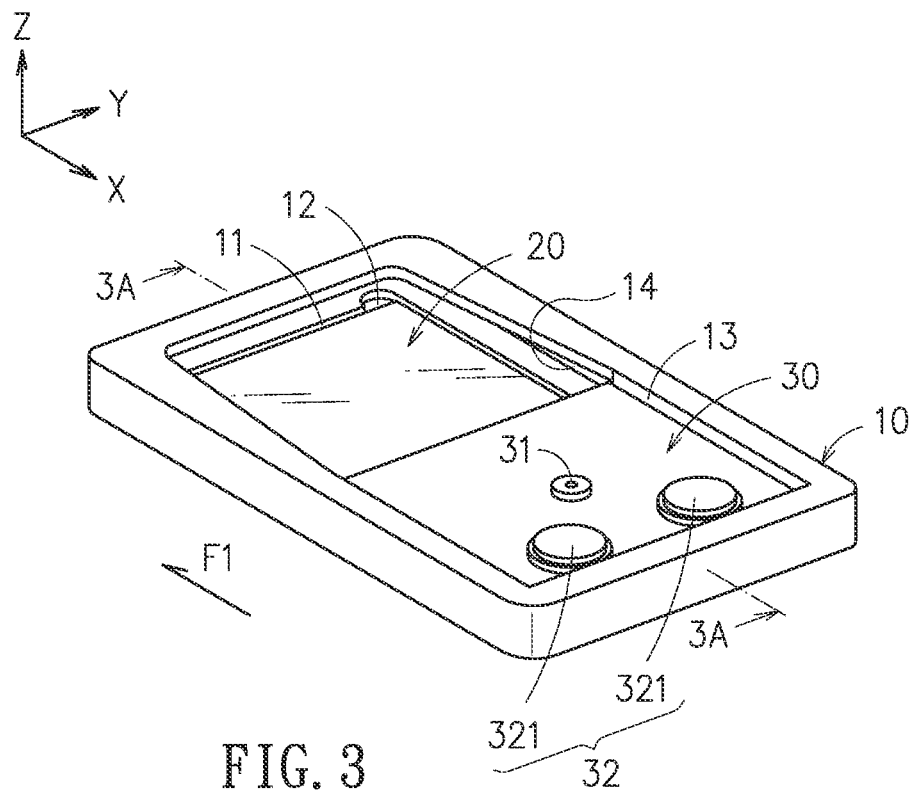
FIG. 3 is a schematic perspective view of FIG. 1 with the sealing film removed and the sliding door plate to be at the second position.
Figure 3A:
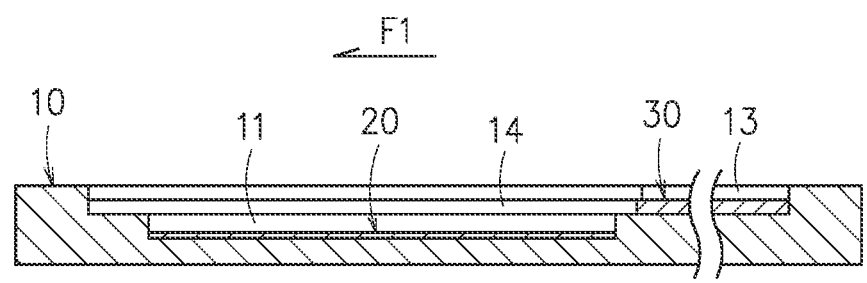
FIG. 3A is a schematic cross-sectional view of FIG. 3 along line 3A-3A.

Referring to FIG. 2, FIG. 3 and FIG. 3A, the container body 10 has a cavity 11 having a protrusive corner 12 at a side thereof, and the protrusive corner 12 is spatially connected with the cavity 11.

The membrane 20 is to be placed into the cavity 11. After the membrane 20 is placed into the cavity 11, an edge of the membrane 20 would be exposed at the protrusive corner 12, such that a gap would exist between the membrane 20 and an inner wall of the protrusive corner 12. With this gap, the membrane 20 can be easily fetched and thus removed from the cavity 11.

The container body 10 has a shallow area 13, and the cavity 11 is disposed in this shallow area 13. At two inner opposite sides of the container body 10 in the shallow area 13 with respect to the cavity 11, a pair of slideways 14 are furnished respectively to extend parallel to a first direction F1.

Referring to FIG. 3, FIG. 3A, FIG. 4 and FIG. 4A, the sliding door plate 30 is provided to slide along the two slideways 14. The sliding door plate 30, parallel to a horizontal level surface as well as the first direction F1, can slide in the first direction F1 between a first position and a second position at an upper portion of the container body 10. Hereinafter, the horizontal level surface would be specifically directed to an X-Y plane spanned by the X and Y axises as shown.

Figure 4:
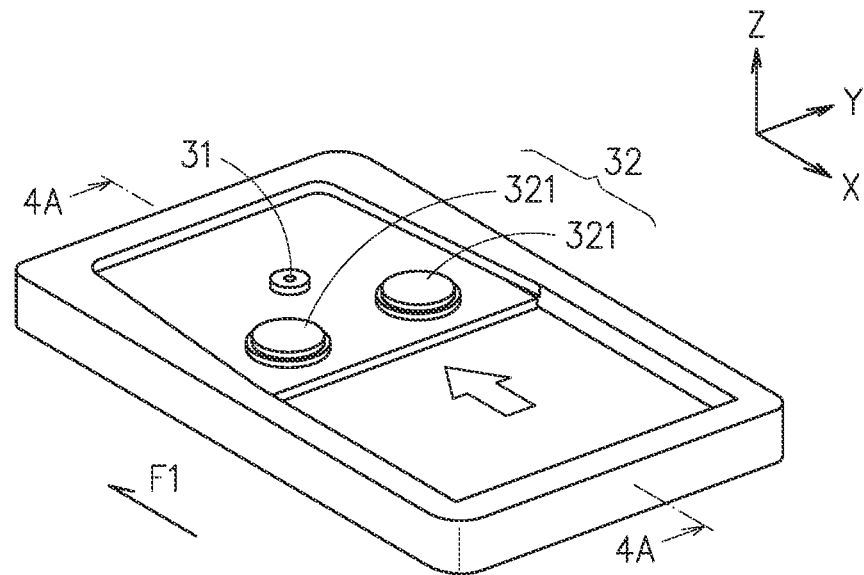
FIG. 4 is a schematic perspective view of FIG. 1 with the sealing film removed and the sliding door plate to be at the first position.

When the sliding door plate 30 is at the second position, the cavity 11 and the membrane 20 can be exposed, as shown in FIG. 3. When the sliding door plate 30 is at the first position, the cavity 11 and the membrane 20 would be covered, as shown in FIG. 4.

Referring to FIG. 3, FIG. 3A, FIG. 4 and FIG. 4A, the sliding door plate 30 includes a hole 31 and a passive magnetic assembly 32.

Figure 4A:
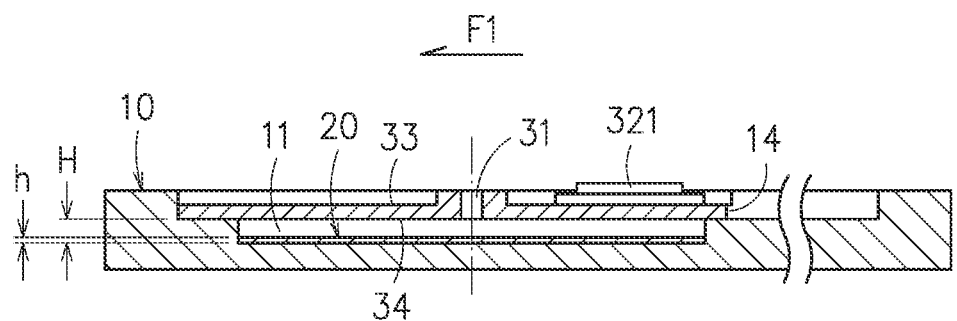
FIG. 4A is a schematic cross-sectional view of FIG. 4 along line 4A-4A.

The hole 31 is configured to penetrate through from a top surface 33 of the sliding door plate 30 to a bottom surface 34 of the sliding door plate 30. When the sliding door plate 30 is at the first position shown in FIG. 4, the hole 31 is located above the cavity 11 and the membrane 20. The hole 31 is configured to allow a solution (not shown in the figure) to enter the cavity 11 from the top surface 33 of the sliding door plate 30. Referring to FIG. 4A, in this embodiment, when the sliding door plate 30 is at the first position, a projection area of the hole 31 is right at a center of the cavity 11 or the membrane 20, such that the introduced solution can be distributed much more uniformly.

In this disclosure, the solution is a mixture of a biocompatible polymer material and cells, in which the polymer material can be one of collagen, gelatin, hyaluronic acid, alginate, PEG and any copolymer the like, and the cells can be one of fibroblasts, myoblasts, epithelial cells, endothelial cells, precursor cells, tenocytes, stem cells, mesenchymal stem cells, bone marrow stem cells and adipose stem cells.

The passive magnetic assembly 32 is adopted to connect magnetically a positive magnetic assembly (not shown in the figure). Driven by the positive magnetic assembly, the sliding door plate 30 having the passive magnetic assembly 32 can slide between the first position and the second position in the first direction F1 and parallel to the horizontal level surface. In this embodiment, the passive magnetic assembly 32 has two passive magnetic elements 321. These two passive magnetic elements 321 are disposed on the same horizontal level surface, and a connection line of these two passive magnetic elements 321 is perpendicular to the first direction F1.

Referring to FIG. 4A, the cavity 11 has a depth H parallel to a Z-axis direction (i.e., perpendicular to the horizontal level surface), and the membrane 20 also has a thickness h parallel to the Z-axis direction and perpendicular to the horizontal level surface. The depth H is larger than the thickness h. The cavity 11 has an area A on the horizontal level surface (i.e., the bottom surface area). Thus, the maximum volume of the solution able to be provided to the cavity 11 is about (H−h)×A. Generally, the thickness h of the membrane 20 is within 10~100 μm. For example, if the membrane 20 has a size of 30×30×0.02 mm, then the solution required is about 0.9~1.1 ml. According to the (H−h)×A, the reference depth H of the cavity 11 can be derived.

Figure 5:
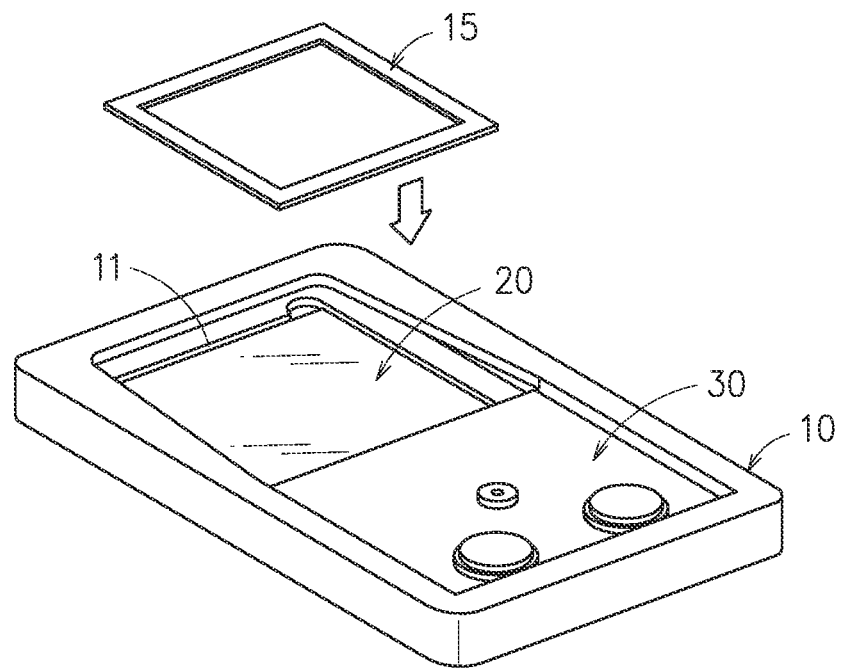
FIG. 5 and FIG. 5A are two schematic perspective view of FIG. 1 having a constraint frame, with the constraint frame separated and engaged, respectively.
Figure 5A:
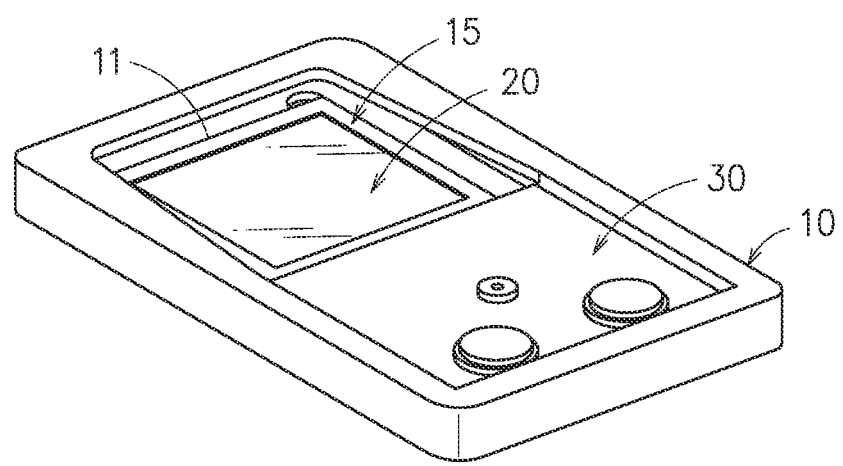

Referring to FIG. 5 and FIG. 5A, in this embodiment, the cavity 11 is furnished with a constraint frame 15. The constraint frame 15 is introduced to tightly fit the cavity 11 so as to fixedly position the membrane 20 thereunder in the cavity 11. With the constraint frame 15 to depress at a circumferential rim of a top surface of the membrane 20, then the membrane 20 can be disposed in the cavity 11 fixedly and stably.

In this disclosure, the constraint frame 15 can be made of one of PET, PS, PP, PVC, PE, PC, ABS, PTFE, rubber and silicon.

Referring to FIG. 1, FIG. 3 and FIG. 4, the membrane 20 and sliding door plate 30 are both disposed in the container body 10 firstly as shown in FIG. 3, then the sliding door plate 30 is moved to the first position for covering the membrane 20 as shown in FIG. 4, and finally the sealing film 40 is applied to cover the sliding door plate 30 and an upper surface of the container body 10 so as to seal the sliding door plate 30 and the membrane 20 inside the sealing film 40. Thereupon, the cell and tissue sheet forming package 100 of FIG. 1 can be formed.

Similarly, in the embodiment of FIG. 5 and FIG. 5A, the sliding door plate 30 and the upper surface of the container body 10 can be sealed by the sealing film 40 in accordance to the arrangement shown in FIG. 3 and FIG. 4. Thus, a package similar to the cell and tissue sheet forming package 100 of FIG. 1 can be obtained.

Figure 6:
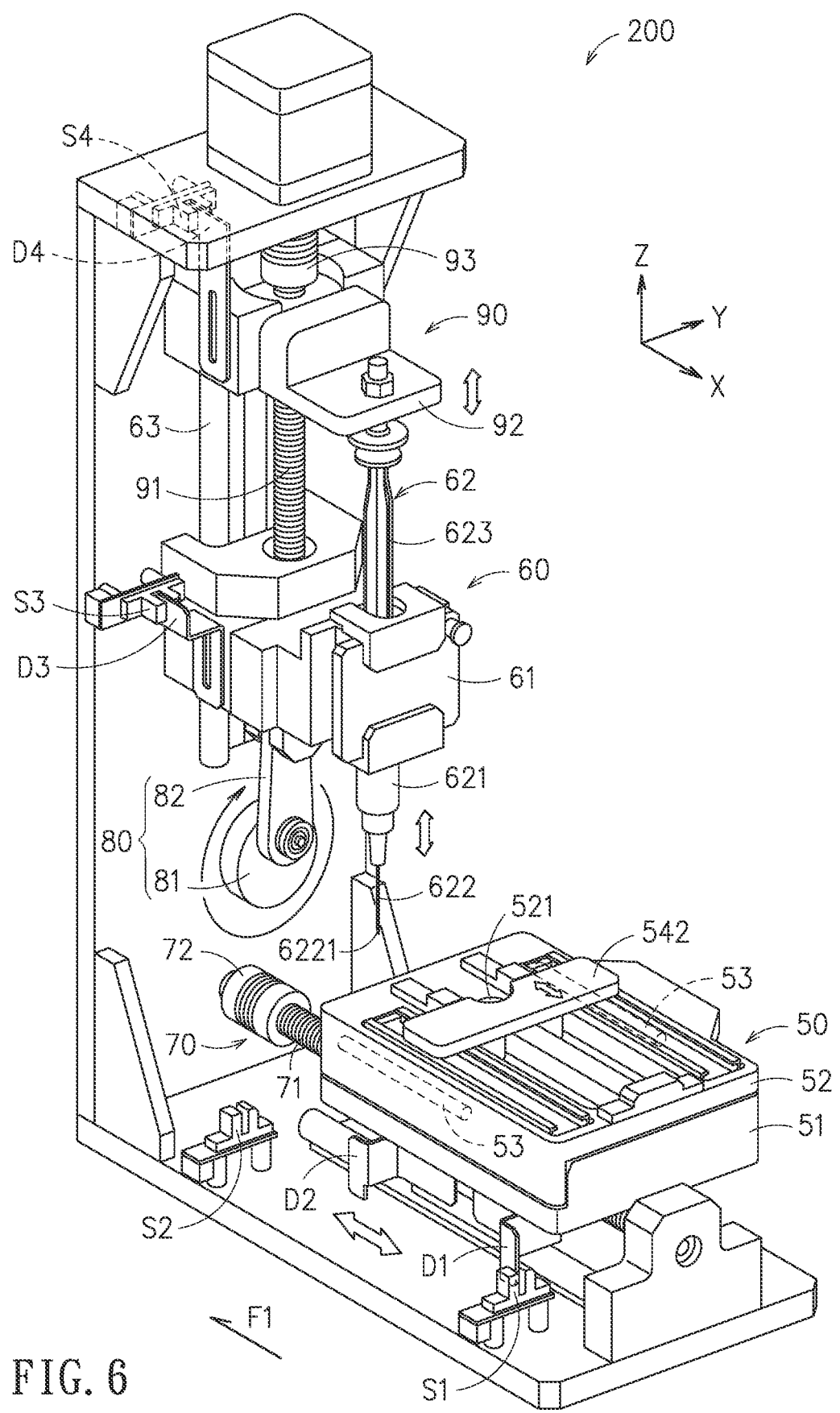
FIG. 6 is a schematic perspective view of an embodiment of the cell injection equipment in accordance with this disclosure.

Referring to FIG. 6, a cell injection equipment 200 is provided to perform the injection of the solution to the cell and tissue sheet forming package 100 of FIG. 1.

The cell injection equipment 200 includes a carrier 50 and an injection mechanism 60. In addition, a drive mechanism consisted of at least a first drive assembly 70, a second drive assembly 80 and a third drive assembly 90 is configured to drive the carrier 50 and the injection mechanism 60.

Figure 7:
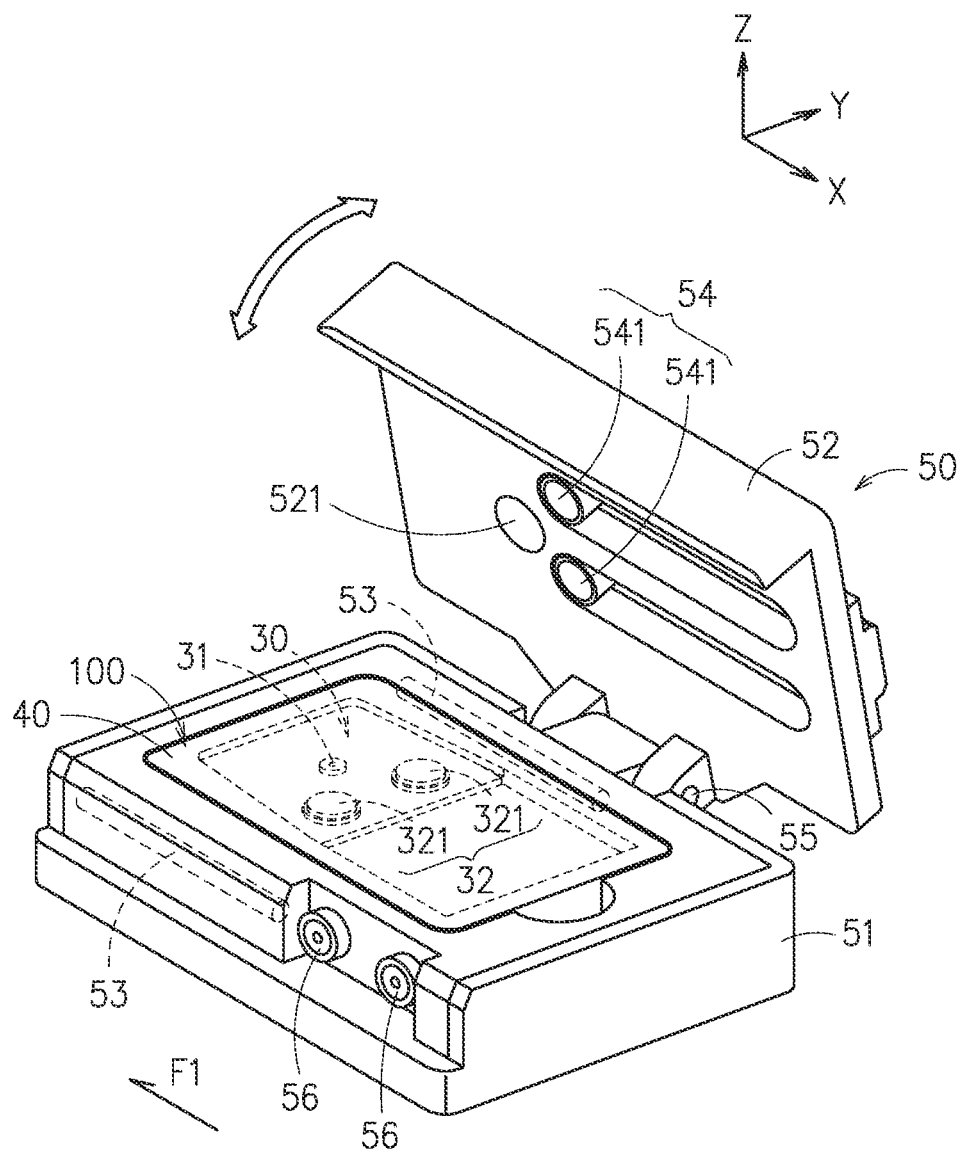
FIG. 7 is a schematic perspective view of an embodiment of the carrier for containing therein the cell and tissue sheet forming package of FIG. 1, with the top block of the carrier opened from the base block thereof.
Figure 8:
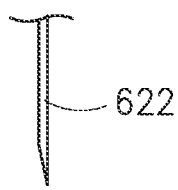
FIG. 8 is a schematic cross-sectional view showing that the carrier is at a fifth position and a projection area of the injection head is deviated from a projection area of the injection hole of the top block in accordance with this disclosure.
Figure 8:
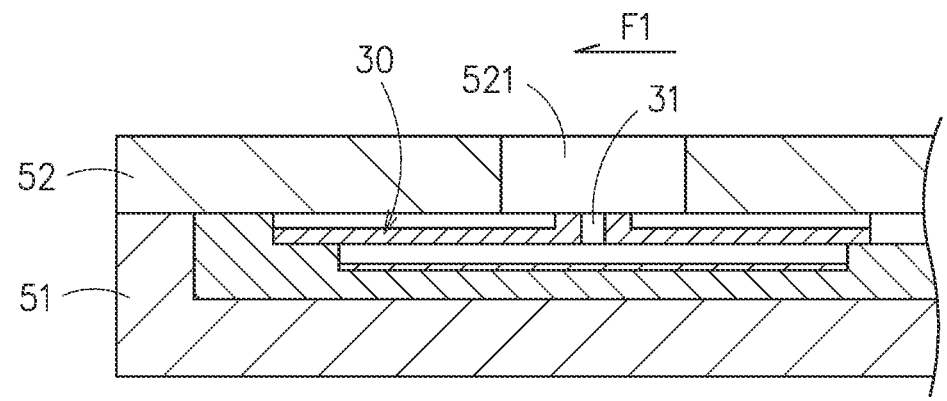

Referring to FIG. 6, FIG. 7 and FIG. 8, the carrier 50 includes a base block 51, a top block 52, two heating elements 53 and a positive magnetic assembly 54.

The base block 51 is relevant to carry the cell and tissue sheet forming package 100 of FIG. 1. The top block 52 is connected with the base block 51. In this embodiment, the top block 52 is connected pivotally with the base block 51 via a hinge 55 at one side thereof. While in an opposite side, at least one magnet member 56 is applied to connect the top block 52 to the base block 51 in a detachable manner, such that the top block 52 can be opened from or closed onto the base block 51. When the top block 52 is closed onto the base block 51, the cell and tissue sheet forming package 100 can be fixedly positioned inside the base block 51. Since the sliding door plate 30 and the other members of the cell and tissue sheet forming package 100 are sealed by the sealing film 40, thus dashed lines thereto are used in FIG. 7. The top block 52 has an injection hole 521. When the top block 52 closes the base block 51, a projection area of the injection hole 521 is overlapping a projection area of the hole 31 of the sliding door plate 30 of the cell and tissue sheet forming package 100, as shown in FIG. 8.

The heating elements 53 are disposed at the base block 51. In this embodiment, two heating elements 53 are shown to two opposite lateral sides of the base block 51, for heating the membrane 20 and the solution of the cell and tissue sheet forming package 100 in between thereof. In this embodiment, each of the heating elements 53 is configured into a tube shape as shown in FIG. 7; but, according to this disclosure, the configuration of the heating element 53 is not limited thereto.

The positive magnetic assembly 54, disposed at the top of the tip block 52, is slidable in the first direction F1 between a third position and a fourth position. The positive magnetic assembly 54 includes two positive magnetic elements 541 connected with a push member 542. When the top block 52 and the base block 51 are in the close state, the two positive magnetic elements 541 of the positive magnetic assembly 54 is right to connect magnetically the two corresponding passive magnetic elements 321 of the passive magnetic assembly 32 at the cell and tissue sheet forming package 100.

Figure 11:
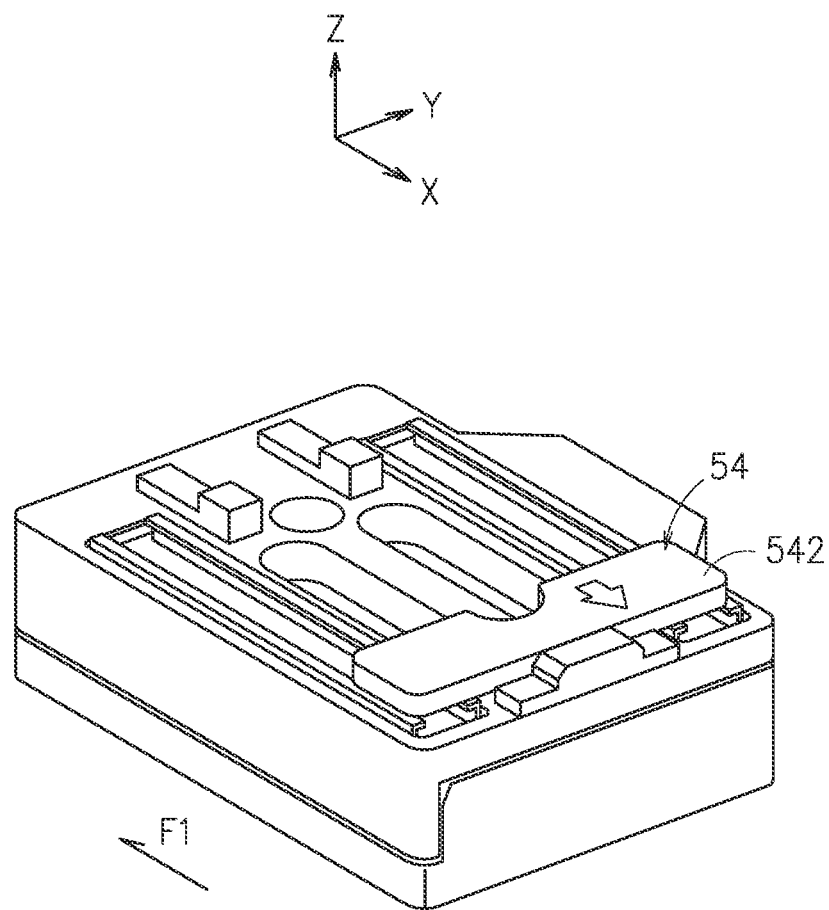
FIG. 11 demonstrates schematically a state that the positive magnetic assembly of the injection device is slided to a fourth position in accordance with this disclosure.

Thereupon, by displacing the push member 542 connected with the two positive magnetic elements 54, the positive magnetic assembly 54 can then slide between the third position and the fourth position (referring to the position of the positive magnetic assembly 54 in FIG. 11). As such, the sliding door plate 30 of the cell and tissue sheet forming package 100 can be then synchronously moved to slide between the first position and the second position (referring to the position of the sliding door plate 30 in FIG. 3).

In this embodiment, with the cell and tissue sheet forming package 100 to be disposed in the carrier 50, the magnetic connection between the positive magnetic assembly 54 and the passive magnetic assembly 32 is utilized to control the movement of the sliding door plate 30 of the cell and tissue sheet forming package 100 outside the carrier 50. In one embodiment, the push member 542 can be also manipulated manually, mechanically or electrically to move the positive magnetic assembly 54 back and forth.

Referring to FIG. 6, the injection mechanism 60 includes a fixing set 61 and an injection assembly 62. The fixing set 61 is mounted to a rack 63 that is extended in parallel to the Z-axis direction but perpendicular to the horizontal level surface.

The injection assembly 62 includes a tube body 621, an injection head 622 and a piston member 623. The tube body 621, formed as a lengthy tube disposed at the fixing set 61, is configured to contain the solution. An axial of the tube body 621 is parallel to the Z-axis direction but perpendicular to the horizontal level surface. The injection head 622, coaxially disposed to a bottom of the tube body 621, has an injection tip 6221 extended toward the horizontal level surface. The piston member 623, axially disposed in the tube body 621, is slidable inside the tube body 621 in the Z-axis direction so as to push out the solution inside the tube body 621 via the injection tip 6221 of the injection head 622.

In the following description, movements of the first drive assembly 70, the second drive assembly 80 and the third drive assembly 90 of the drive mechanism will be elucidated.

Figure 8A:
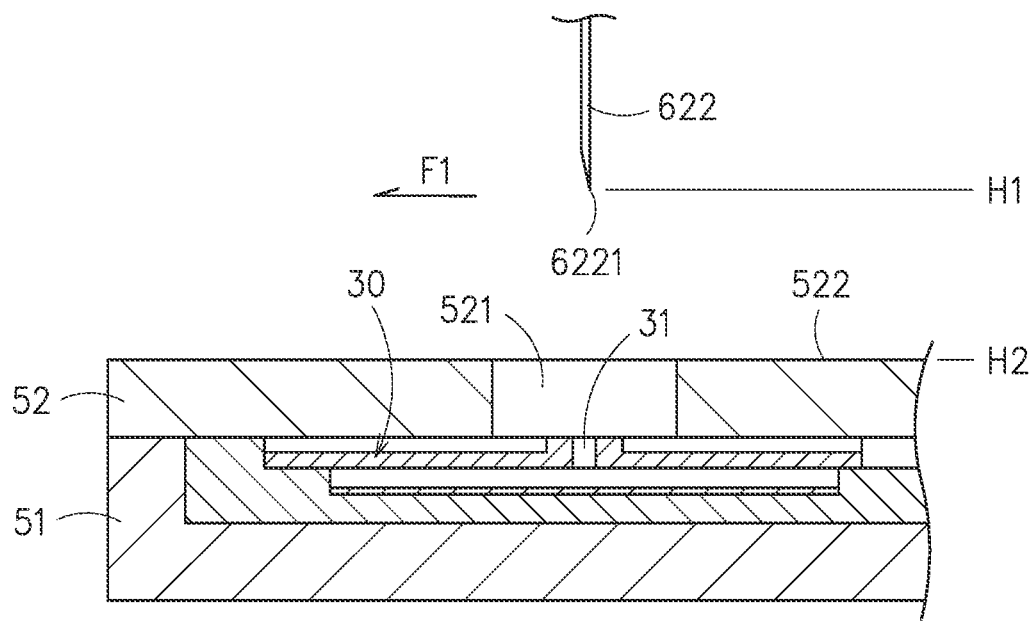
FIG. 8A is a schematic cross-sectional view showing that the carrier is at a sixth position and a projection area of the injection head 622 is coincided with a projection area of the injection hole of the top block in accordance with this disclosure.

Referring to FIG. 6, FIG. 8 and FIG. 8A, the first drive assembly 70 is utilized to displace the carrier 50, particularly to move in the first direction F1 by being parallel to the horizontal level surface. The first drive assembly 70 includes a first screw bar 71 and a first motor 72. An axial direction of the first screw bar 71 is parallel to the horizontal level surface, and the carrier 50 is disposed to the first screw bar 71. The first motor 72 is to rotate the first screw bar 71 clockwise and counter clockwise, and thereby to synchronously drive the carrier 50 to undergo a reciprocating movement between a fifth position and a sixth position.

A first sensor S1 and a second sensor S2 are located at a side of the carrier 50, and a first detection plate D1 and a second detection plate D2 are provided to the base block 51 of the carrier 50 at positions of the same side thereof in correspondence to the first sensor S1 and the second sensor S2, respectively. The first detection plate D1 and the second detection plate D2 are to be detected by the first sensor S1 and the second sensor S2, respectively, so as to capture position information of the carrier 50. When the first drive assembly 70 drives the carrier 50 to displace, the first detection plate D1 and the second detection plate D2 would move along with the carrier 50 synchronously. If the carrier 50 is moved, then the first detection plate D1 and the second detection plate D2 would gradually enter detection ranges of the first sensor S1 and the second sensor S1, such that the carrier 50 can be controlled to stop at the fifth position or the sixth position.

As soon as the first sensor S1 detects the first detection plate D1, then the first drive assembly 70 would be controlled to stop so as to have the carrier 50 to stop at the fifth position, as shown in FIG. 6. At this time, the projection area of the injection head 622 would be deviated from the projection area of the injection hole 521 of the top block 52, as shown in FIG. 8.

Referring to FIG. 6, when the first drive assembly 70 drives the carrier 50 to move toward one side of the injection mechanism 60 so as to have the second sensor S2 to detect the second detection plate D2, then the first drive assembly 70 is controlled to stop the carrier 50 at the sixth position. At this time the projection area of the injection head 622, that of the injection hole 521 of the top block 52, and that of the hole 31 of the sliding door plate 30 would be coincided, as shown in FIG. 8A. Then, the second drive assembly 80 can proceed to drive the fixing set 61 and the injection assembly 62 to move.

Referring to FIG. 6, the second drive assembly 80 is to drive the fixing set 61 and the injection assembly 62 to move. The second drive assembly 80 includes a cam member 81, a link member 82 and a drive member (not shown in the figure), in which the drive member can be a motor. The cam member 81 is disposed under the fixing set 61. One end of the link member 82 is pivotally connected to the fixing set 61, while another end thereof is pivotally connected to an eccentric point of the cam member 81. When the drive member rotates the cam member 81, the link member 82 would be driven synchronously to move the fixing set 61. In this embodiment, the fixing set 61 and the injection assembly 62 would undergo a reciprocating movement between a seventh position and an eighth position, parallel to the Z-axis direction along the rack 63, and perpendicular to the horizontal level surface.

A third sensor S3 is located beside the injection mechanism 60, and a third detection plate D3 to be detected by the third sensor S3 so as for obtaining the position information of the fixing set 61 and the injection assembly 62 of the injection device 60 is provided to the fixing set 61 at the same side where the third sensor S3 is located. When the second drive assembly 80 drives the fixing set 61 and the injection assembly 62 to move, the third detection plate D3 may move synchronously so as further to enter a detection range of the third sensor S3. When the third sensor S3 detects the third detection plate D3, then the second drive assembly 80 is controlled to stop so as to have the fixing set 61 stopped at the seventh position, as shown in FIG. 6. At this time, as shown in FIG. 8A, the horizontal position H1 of the injection tip 6221 is higher than the horizontal position H2 of the tip surface 522 of the top block 52 of the carrier 50.

Figure 9:
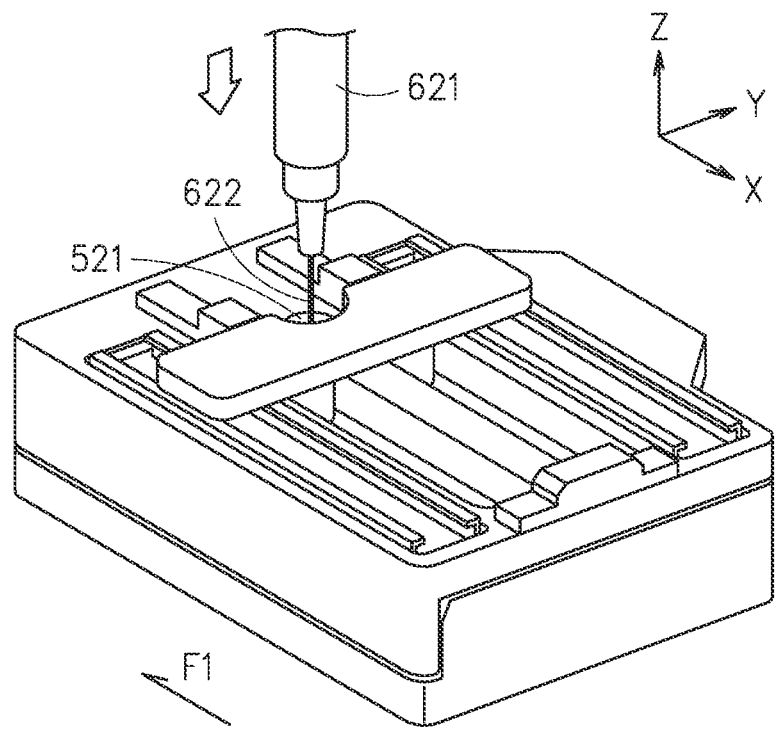
FIG. 9 demonstrates schematically a state that the injection assembly of the injection device is lowered to an eighth position in accordance with this disclosure.
Figure 9A:
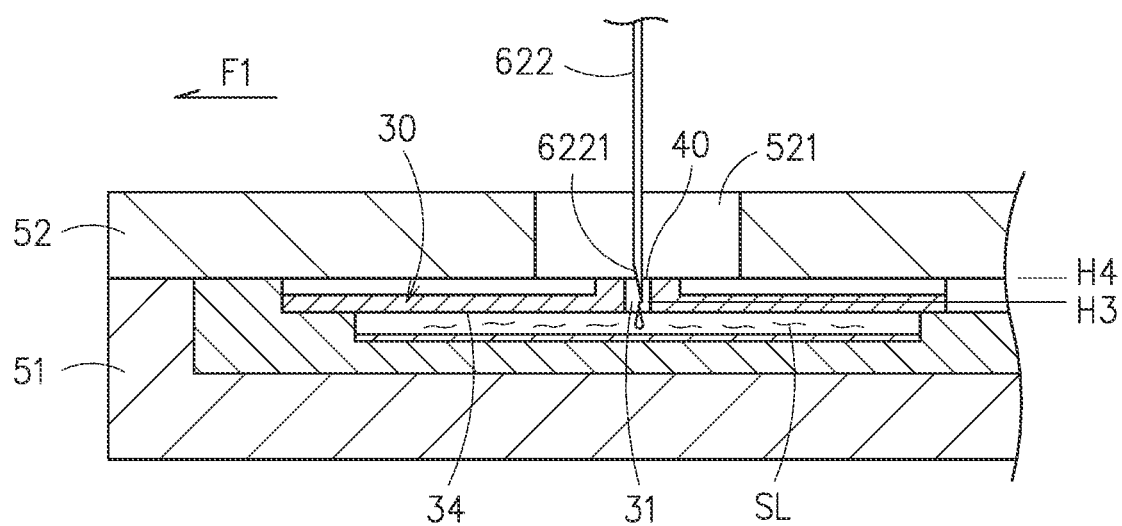
FIG. 9A is a schematic cross-sectional view showing that a horizontal position of the injection tip of the injection device is lower than a horizontal position of the bottom surface of the sliding door plate in accordance with this disclosure.

Referring to FIG. 6, FIG. 9 and FIG. 9A, when the fixing set 61 and the injection assembly 62 are driven downward to the eighth position, the injection head 622 would enter the injection hole 521. Since the horizontal position H3 of the injection tip 6221 is lower than the horizontal position H4 of the sealing film 40 at the top of the hole 31, and the projection area of the injection head 622 and that of the injection hole 521 of the top block 52 are overlapped, thus the injection tip 6221 can pierce the sealing film 40 to enter the hole 31. Then, the third drive assembly 90 can be activated to depress the piston member 623 of the injection assembly 62.

Referring to FIG. 6, the third drive assembly 90 is configured to move the piston member 623. The third drive assembly 90 includes a second screw bar 91, a depression member 92 and a second motor 93. An axial direction of the second screw bar 91 is parallel to the Z-axis direction but perpendicular to the horizontal level surface. The depression member 92, disposed to the second screw bar 91, has a lower side to face a top surface of the piston member 623, in which the lower side is used to directly depress the piston member 623. The second motor 93 can drive the second screw bar 91 to rotate clockwise and counter clockwise so as to synchronously displace the depression member 92 linearly in a reciprocating manner between a ninth position and a tenth position, by being parallel to the Z-axis direction but perpendicular to the horizontal level surface.

One side of the cell injection equipment 200 is further furnished with a fourth sensor S4, and, at the same side, the depression member 92 of the third drive assembly 90 is provided with a fourth detection plate D4 to pair the fourth sensor S4. The fourth detection plate D4 is used to be detected by the fourth sensor S4 so as to obtain the position information of the depression member 92. When the third drive assembly 90 drives the depression member 92 to move, the fourth detection plate D4 would displace synchronously to approach the detection range of the fourth sensor S4. In FIG. 6, the depression member 92 is shown to be at the ninth position where the fourth sensor S4 can detect the fourth detection plate D4, and then the third drive assembly 90 is controlled to stop. At this time, the depression member 92 does not contact the piston member 623, and the fixing set 61 is at the seventh position.

Referring to FIG. 9 and FIG. 9A, when the second drive assembly 80 drives the fixing set 61 and the injection assembly 62 to move downward to the eighth position as shown in FIG. 9 and FIG. 9A, the third drive assembly 90 would then lower the depression member 92 in the Z-axis direction but perpendicular to the horizontal level surface, such that the depression member 92 can contact the piston member 623. With the depression member 92 continues to reach the tenth position so as to push out the solution SL originally inside the tube body 621 via the injection head 622, then the solution SL would enter the space between the sliding door plate 30 and the membrane 20, as shown in FIG. 9A.

Figure 10:
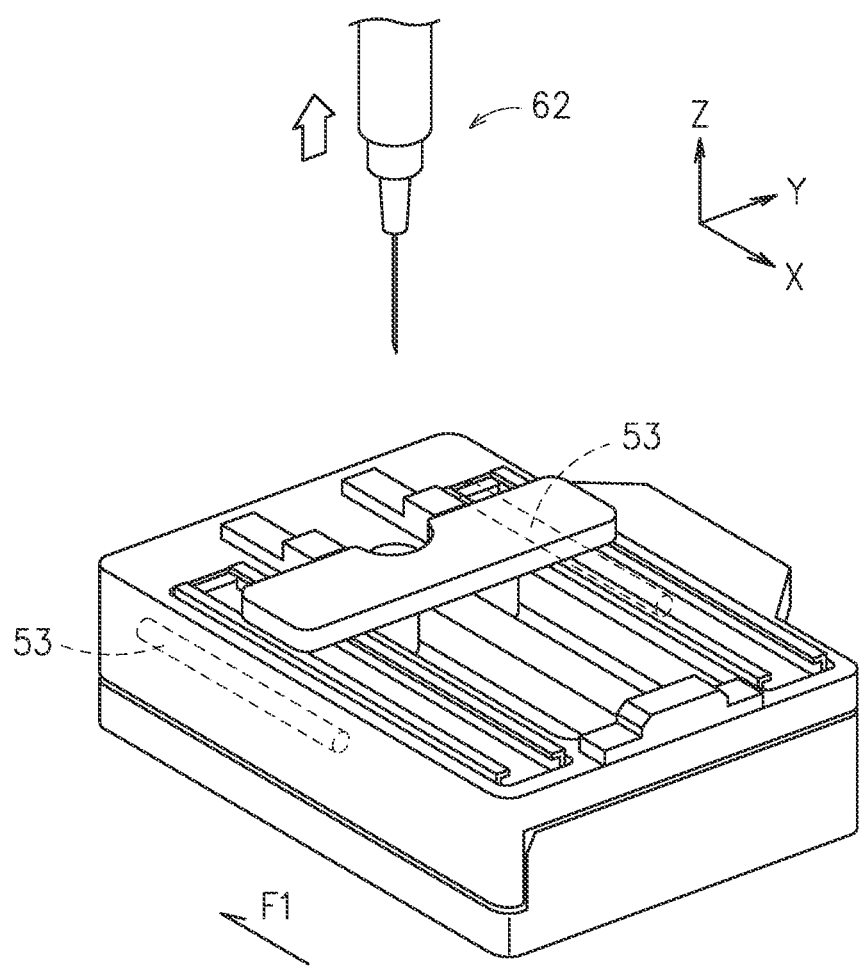
FIG. 10 demonstrates schematically a state that the injection assembly of the injection device is raised to a seventh position and the heating element is heating in accordance with this disclosure.

Referring to FIG. 6, FIG. 9A and FIG. 10, after the solution SL is completely injected into the space between the sliding door plate 30 and the membrane 20, the third drive assembly 90 would drive the depression member 92 upward to retrieve from the contact of the piston member 623. When the depression member 92 is raised to the ninth position as shown in FIG. 6, the fourth sensor S4 would detect the fourth detection plate D4, and the third drive assembly 90 would be controlled to stop.

Then, the second drive assembly 80 is controlled to drive the fixing set 61 and the injection assembly 62 upward to the seventh position as shown in FIG. 6. When the third sensor S3 detects the third detection plate D3, the second drive assembly 80 is controlled to stop, such that the fixing set 61 can stop at the seventh position, as shown in FIG. 6.

Then, the heating element 53 would provide thermal energy to the membrane 20 and the solution SL of the cell and tissue sheet forming package 100, such that the solution SL can be transformed into a colloid sheet 21 attached to the membrane 20. In one embodiment, to a 30×30×0.02 mm membrane 20 and a 0.9~1.1 ml solution SL, if the heating element 53 is heated up to 37~40° C., then about 10 minutes are enough for the solution SL to form the colloid sheet 21 attached on the membrane 20.

Then, as shown in FIG. 11, by moving the push member 542 in the first direction F1, the positive magnetic assembly 54 can be slided to the fourth position. Since the two positive magnetic elements 541 of the positive magnetic assembly 54 can be connected magnetically with the two passive magnetic elements 321 of the passive magnetic assembly 32 of the cell and tissue sheet forming package 100, thus the sliding door plate 30 can be synchronously slided to the second position (referring to FIG. 3 for the position of the sliding door plate 30). In addition, since the sliding door plate 30 is moved by sliding, thus any adhesive from the colloid sheet 21 on the membrane 20 can be avoided.

Figure 12:
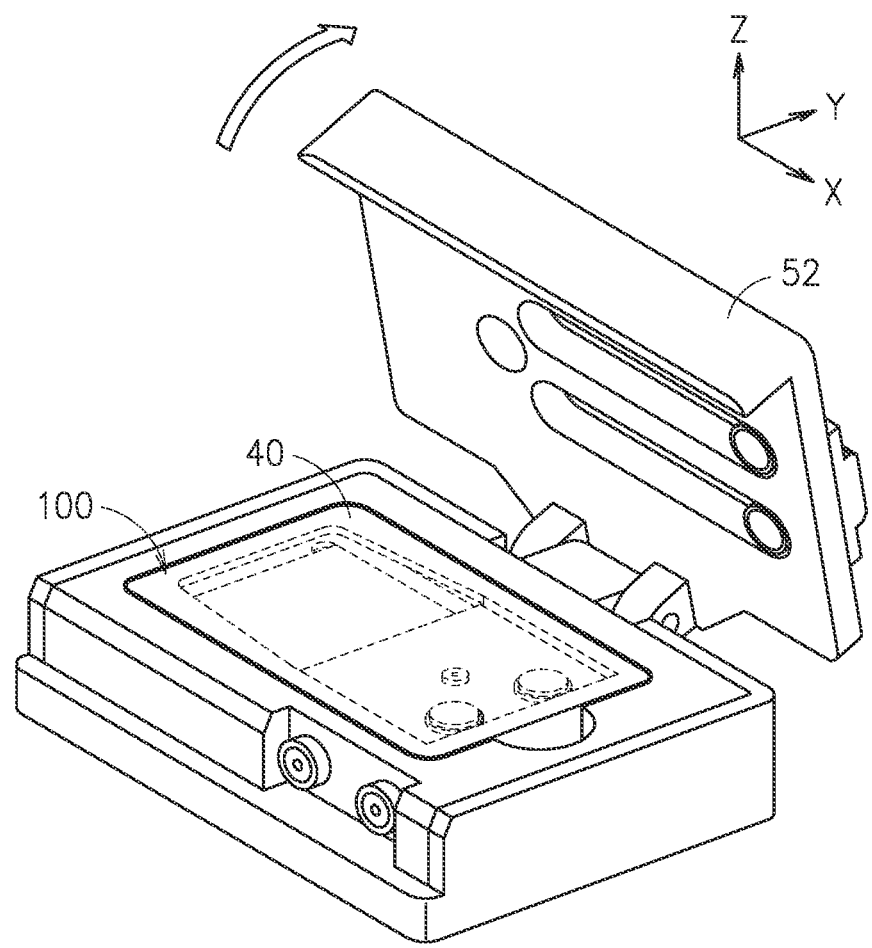
FIG. 12 demonstrates schematically a state that the top block of the injection device is opened and the cell and the tissue sheet forming package is ready to be fetched in accordance with this disclosure.

Then, as shown in FIG. 12, after the top block 52 is opened, the cell and tissue sheet forming package 100 can be fetched out from the base block 51, and thus the sealing film 40 wrapping the cell and tissue sheet forming package 100 can be peeled off.

Figure 13:
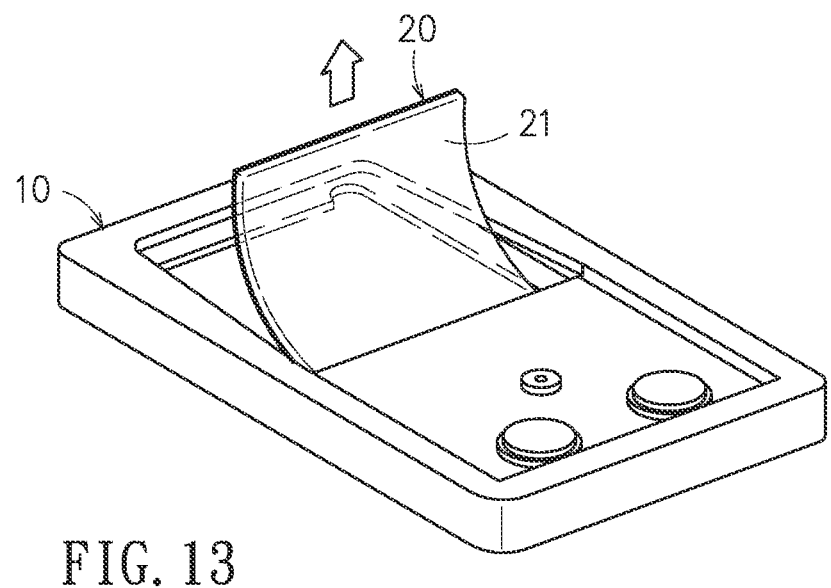
FIG. 13 demonstrates schematically a state that the cell and tissue sheet is removing from the cell and tissue sheet forming package in accordance with this disclosure.

Further, as shown in FIG. 13, the membrane 20 attached thereon with the colloid sheet 21 (i.e., the cell and tissue sheet) can be removed from the container body 10 for a direct treatment on a wound.

Figure 14:
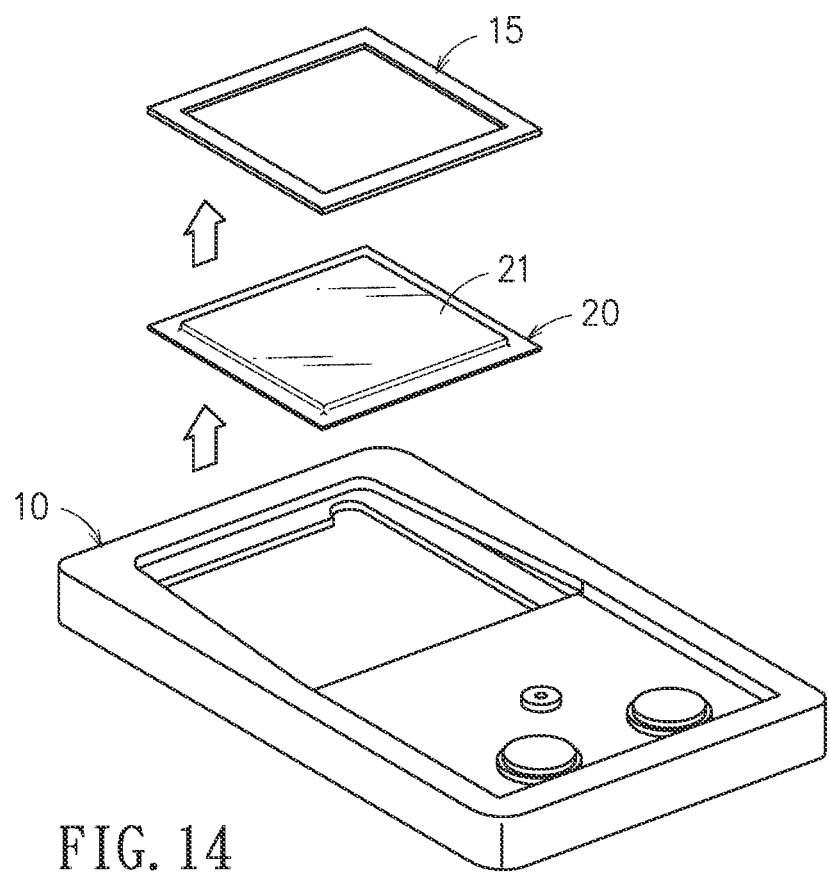
FIG. 14 demonstrates schematically a state that the cell and tissue sheet is removed from the cell and tissue sheet forming package furnished with the constraint frame in accordance with this disclosure.

If the constraint frame 15 of FIG. 5 and FIG. 5A is applied on the membrane 20, then, as shown in FIG. 14, both the constraint frame 15 and the membrane 20 attached thereon with the colloid sheet 21 are removed together from the container body 10. Then, the constraint frame 15 and the membrane 20 with the colloid sheet 21 are separated, and the membrane 20 with the colloid sheet 21 attached thereon (i.e., the cell and tissue sheet) can be directly applied on a wound of a patient.

In summary, by providing the cell and tissue sheet forming package and cell injection equipment of this disclosure, the membrane is pre-sealed inside the cell and tissue sheet forming package. Thus, when a cell and tissue sheet is required, the cell and tissue sheet forming package is placed into the carrier of the cell injection equipment by the on-site medical personnel. Then, the injection assembly having the solution prepared by mixing cells and the predetermined polymer material can be mounted onto the injection mechanism of the cell injection equipment. As the cell injection equipment is turned on, the carrier can be moved to the position under the injection mechanism, and then the injection assembly is lowered to inject the solution into the cell and tissue sheet forming package. After necessary heating, the magnetic assemblies can be applied to slide the sliding door plate away from the cell and tissue sheet forming package, and then the membrane having thereon the colloid sheet (i.e., the cell and tissue sheet) can be removed directly for further treatment.

As described above, empirically, to a 30×30×0.02 mm membrane 20 and a 0.9~1.1 ml solution SL, with the heating element 53 to heat up to 37~40° C. for about 10 minutes, then the solution SL can be transformed into the colloid sheet 21 attached on the membrane 20. In accordance with this disclosure, the cell treatment procedures can be significantly simplified, no tedious operation in the laboratory for culturing the cells and forming the cell sheets is necessary, and thus the risk in temperature control while transporting the cell products can be avoided. With the pre-prepared package and the cell injection equipment, the cell sheets can be produced on-site in the clinic. By peeling the sterile package, the cell and tissue sheet thereinside can be directly applied to the patient, and thus the entire treatment can be substantially shortened and simplified.

With respect to the above description then, it is to be realized that the optimum dimensional relationships for the parts of the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

What is claimed is:

1. A cell and tissue sheet forming package, comprising:
a container body, having a cavity;
a membrane, disposed in the cavity, made of a hydrophilic material; and
a sliding door plate, disposed slidably at a top of the container body in a manner of being parallel to a horizontal level surface and a first direction, the sliding door plate being slidable between a first position and a second position at the top; wherein, when the sliding door plate is at the first position, the sliding door plate covers the cavity and the membrane; wherein, when the sliding door plate is at the second position, the cavity and the membrane are exposed; the sliding door plate including:
a hole, penetrating from a top surface of the sliding door plate to a bottom surface of the sliding door plate; wherein, when the sliding door plate is at the first position, the hole is positioned above the cavity and the membrane for a solution to be injected therethrough into the cavity from the top surface of the sliding door plate; and
a passive magnetic assembly, disposed at the sliding door plate for connecting magnetically a positive magnetic assembly, the positive magnetic assembly being configured to slide the sliding door plate; and
a sealing film, configured to cover the sliding door plate and the container body so as to seal the sliding door plate and the membrane.

2. The cell and tissue sheet forming package of claim 1, further including a constraint frame configured to fit tightly the cavity and thus able to depress on a circumferential rim of the membrane.

3. The cell and tissue sheet forming package of claim 1, wherein a depth of the cavity is greater than a thickness of the membrane.

4. The cell and tissue sheet forming package of claim 1, wherein the cavity has a depth H perpendicular to the horizontal level surface, the membrane has a thickness h perpendicular to the horizontal level surface, the cavity has an area A parallel to the horizontal level surface, and a maximum volume of the solution is $(H-h) \times A$.

5. The cell and tissue sheet forming package of claim 1, wherein the container body has a shallow area, the cavity is disposed in the shallow area, two slideways are furnished to opposite sides of the shallow area in correspondence to the cavity, the two slideways are individually extended in the first direction, and the sliding door plate is disposed between the two slideways.

6. The cell and tissue sheet forming package of claim 1, wherein the cavity further has a protrusive corner, the protrusive corner and the cavity are connected spatially, and an edge of the membrane is exposed to the protrusive corner so as to produce a gap between the membrane and the protrusive corner.

7. The cell and tissue sheet forming package of claim 1, wherein, when the sliding door plate is at the first position, a projection area of the hole is coincided with centers of the cavity and the membrane.

8. The cell and tissue sheet forming package of claim 1, wherein the passive magnetic assembly has two passive magnetic elements parallel to the horizontal level surface, and a line connecting the two passive magnetic elements is perpendicular to the first direction.

9. The cell and tissue sheet forming package of claim 1, wherein the solution is a mixture of a biocompatible polymer material and cells.

10. The cell and tissue sheet forming package of claim 9, wherein the polymer material is one of collagen, gelatin, hyaluronic acid, alginate, and PEG.

11. The cell and tissue sheet forming package of claim 9, wherein the cells are one of fibroblasts, myoblasts, epithelial cells, endothelial cells, precursor cells, tenocytes, stem cells, mesenchymal stem cells, bone marrow stem cells and adipose stem cells.

* * * * *